(12) United States Patent
Butler et al.

(10) Patent No.: US 9,268,125 B2
(45) Date of Patent: Feb. 23, 2016

(54) RETRACTABLE BEAM SPLITTER FOR MICROSCOPE

(71) Applicant: Endure Medical, Inc., Cumming, GA (US)

(72) Inventors: Jonathan Michael Butler, Gainsville, GA (US); Robert Troy Hewlett, Cumming, GA (US); Robert Jeffrey Hewlett, Dawsonville, GA (US); Robert McCoy Hewlett, Cumming, GA (US)

(73) Assignee: Alcon Research, Ltd., Fort Worth, TX (US)

( * ) Notice: Subject to any disclaimer, the term of this patent is extended or adjusted under 35 U.S.C. 154(b) by 226 days.

(21) Appl. No.: 14/043,307

(22) Filed: Oct. 1, 2013

(65) Prior Publication Data

US 2014/0029090 A1 Jan. 30, 2014

Related U.S. Application Data

(63) Continuation of application No. 13/685,173, filed on Nov. 26, 2012, now Pat. No. 8,573,808, which is a continuation of application No. 13/216,178, filed on Aug. 23, 2011, now Pat. No. 8,337,047, which is a continuation-in-part of application No. 12/267,380, filed on Nov. 7, 2008, now Pat. No. 8,177,394.

(51) Int. Cl.

| | |
|---|---|
| *G02B 21/06* | (2006.01) |
| *G02B 21/00* | (2006.01) |
| *G02B 21/08* | (2006.01) |
| *G02B 21/22* | (2006.01) |
| *G02B 27/12* | (2006.01) |
| *A61F 9/007* | (2006.01) |

(52) U.S. Cl.
CPC ............ *G02B 21/06* (2013.01); *G02B 21/0012* (2013.01); *G02B 21/082* (2013.01); *A61F 9/00727* (2013.01); *G02B 21/22* (2013.01); *G02B 27/126* (2013.01)

(58) Field of Classification Search
USPC .................... 362/253, 234, 572; 359/385, 389
See application file for complete search history.

(56) References Cited

U.S. PATENT DOCUMENTS

| | | | |
|---|---|---|---|
| 4,779,968 A | 10/1988 | Sander | |
| 6,186,628 B1 | 2/2001 | de Velde | |
| 2003/0048528 A1 | 3/2003 | Deverin | |
| 2004/0246575 A1 | 12/2004 | Tonooka | |
| 2007/0135805 A1 | 6/2007 | Peyman | |
| 2008/0266656 A1 | 10/2008 | Sander | |
| 2010/0118549 A1 | 5/2010 | Butler | |
| 2011/0077734 A1 | 3/2011 | Grierson et al. | |
| 2012/0147460 A1* | 6/2012 | Kubler .................... | A61B 3/13 359/389 |

FOREIGN PATENT DOCUMENTS

| | | |
|---|---|---|
| JP | 6327810 | 2/1988 |
| JP | 08280629 | 10/1996 |
| JP | 10133122 | 5/1998 |

(Continued)

*Primary Examiner* — Laura Tso

(57) ABSTRACT

Systems and methods are provided for illuminating a surface to be observed microscopically using a retractable beamsplitter. The retractable beamsplitter allows the use of coaxial illumination when the beamsplitter is positioned in the operator's line of sight. The retractable beamsplitter allows the use of non-coaxial illumination without reducing the amount of illumination that reaches the operator when the beamsplitter is retracted from the operator's line of sight. As a result a single system can be used effectively to provide various types of illumination.

14 Claims, 14 Drawing Sheets

(56) References Cited

FOREIGN PATENT DOCUMENTS

| | | |
|---|---|---|
| JP | 2011326773 | 11/1999 |
| JP | 2004085796 A | 3/2004 |
| JP | 2005227371 | 8/2005 |
| JP | 200840306 | 2/2008 |
| JP | 200868942 | 3/2008 |
| JP | 09297073 | 12/2009 |

* cited by examiner

RETRACTABLE BEAM SPLITTER FOR MICROSCOPE

RELATED APPLICATIONS

This application is a continuation of U.S. patent application Ser. No. 13/685,173, filed on Nov. 26, 2012, which is incorporated herein by reference and which is a continuation of U.S. patent application Ser. No. 13/216,178, filed on Aug. 23, 2011, now granted U.S. Pat. No. 8,337,047, which is incorporated herein by reference and which is a continuation-in-part of U.S. patent application Ser. No. 12/267,380, filed on Nov. 7, 2008, now granted U.S. Pat. No. 8,177,394, which is incorporated herein by reference.

CROSS-REFERENCE TO RELATED APPLICATIONS

This application is a continuation of U.S. application Ser. No. 13/216,178, filed on Aug. 23, 2011, which is currently pending. U.S. application Ser. No. 13/216,178 is a continuation-in-part of U.S. patent application Ser. No. 12/267,380, filed on Nov. 7, 2008, which was issued as U.S. Pat. No. 8,177,394 on May 15, 2012. The contents of U.S. application Ser. Nos. 13/216,178 and 12/267,380 are incorporated herein by reference in their entireties.

FIELD OF THE DISCLOSURE

The present disclosure is in the field of microscopes.

BACKGROUND

This disclosure refers to various outside documents to aid the reader in understanding the embodiments of the processes, machines, manufactures, compositions of matter, and other teachings of the present disclosure; to enable those of ordinary skill in the art to practice the embodiments of the processes, machines, manufactures, compositions of matter, and other teachings of the present disclosure; and to allow one of ordinary skill in the art to understand the metes and bounds of the embodiments of the processes, machines, manufactures, compositions of matter, and other teachings of the present disclosure. No admission is made that any such document meets any legal definition of "prior art" in any country, and the Applicants reserve the right to demonstrate that any such document meets or fails to meet any legal definition of "prior art" in any country. All such documents are incorporated by reference herein so far as is necessary to enable those of ordinary skill in the art to practice the embodiments of the processes, machines, manufactures, compositions of matter, and other teachings of the present disclosure; and to allow one of ordinary skill in the art to understand the metes and bounds of the embodiments of the processes, machines, manufactures, compositions of matter, and other teachings of the present disclosure.

In the surgical setting, there have been a number of different microscopes designed and sold for ophthalmic surgery. Presently there are no microscopes that deliver two collimated light beams in stereoscopic to the subject surface, e.g., the tissue under examination in a surgical procedure.

Until now microscopes have delivered to the subject surface (1) one or more uncollimated light beams from the objective lens or (2) a single uncollimated light beam below the objective. Routing a parallel light beam through the objective lens transmits a light beam which is not collimated. The illumination system, described in U.S. Pat. No. 4,779,968 delivered a single uncollimated light beam from a single light source to the subject surface through objective lens (shown as 1 or 1a), wherein FIGS. 1 and 3 of U.S. Pat. No. 4,779,968 depict the beam to the subject surface passing through an objective lens which is uncollimated. Another illumination system believed to be from the Zeiss Lumera microscope delivered two focused (uncollimated) beams to the subject surface through the objective lens. Another illumination system from the Moller EOS 900 microscope delivered two focused (uncollimated) light beams through the objective lens to the subject surface.

U.S. patent publication 2010/0118549, published May 13, 2010, describes an invention directed toward cataract surgery in which the microscope light reflects from the retina to produce a red reflex, in essence a backlighting of the lens in cataract surgery.

Illumination in retinal surgery is different from that in cataract surgery. In retinal surgery the microscope is equipped with a device for magnifying the retina so that the surgeon sees a large view of the operative site. However, the illumination of the surgical microscope for cataract surgery is not used in retinal surgery. In retinal surgery, a small fiber-optic pic about 1 mm in diameter is inserted through the sclera and into the vitreous body for direct illumination of the retinal surface. The surgeon holds this fiber-optic pic such that light exiting the tip of the fiber-optic pic is directed toward the retinal tissue on which the operating instruments are utilized.

SUMMARY

Microscopes are used in many different fields. The systems of the present disclosure can be used in any field but are especially useful in surgical settings or any other application in which highly three dimensional objects require magnification, particularly those partially occluded by an enclosure. An example of this is ophthalmic surgery The illumination system of the present disclosure allows delivery of two collimated light beams to the subject surface which at least partially overlap, producing stereoscopic illumination. Additionally, an independent system of illumination may be provided at an angle oblique to the stereoscopic system. Either system can be used together or separately.

As defined herein and unless otherwise stated, (a) "collimated light" means light rays from any light source which are partially parallel instead of converging or diverging; and (b) "collimation" means the process of arranging converging or diverging light beams so that they are at least partially parallel. If the light source for each stereoscopic beam was truly a point source there would be little overlap of the beams on the subject surface. With a white light source the focal length of the lens varies with wavelength. An ideally collimated beam would result from a monochromatic point source located at the focal point of the condenser lens. The larger the light source, however, the more other effects occur. Light from one side of the bulb, for example, enters the condenser lens at a different point than light from the bulb's other side and therefore they behave differently as they exit the lens. Light that lies directly on the optical axis of the lens is collimated but the off axis light creates some divergence in the beams.

Certain embodiments of the illumination system incorporate a 50%/50% beamsplitter plate. The beamsplitter plate facilitates red reflex enhancement during cataract surgery on the lens, but is not necessary for retinal surgery. In fact, its presence can reduce 50% of the light returning from the surgical site to the surgeon's eyes. It is therefore desirable to remove the beamsplitter plate from the optical system for retinal surgery. In certain embodiments of the system this is accomplished by allowing the beamsplitter plate to be removed from the light beam path, thus allowing 100% of the reflected light from the retina to enter the optical system of the surgical microscope.

DETAILED DESCRIPTION

Figure 1:
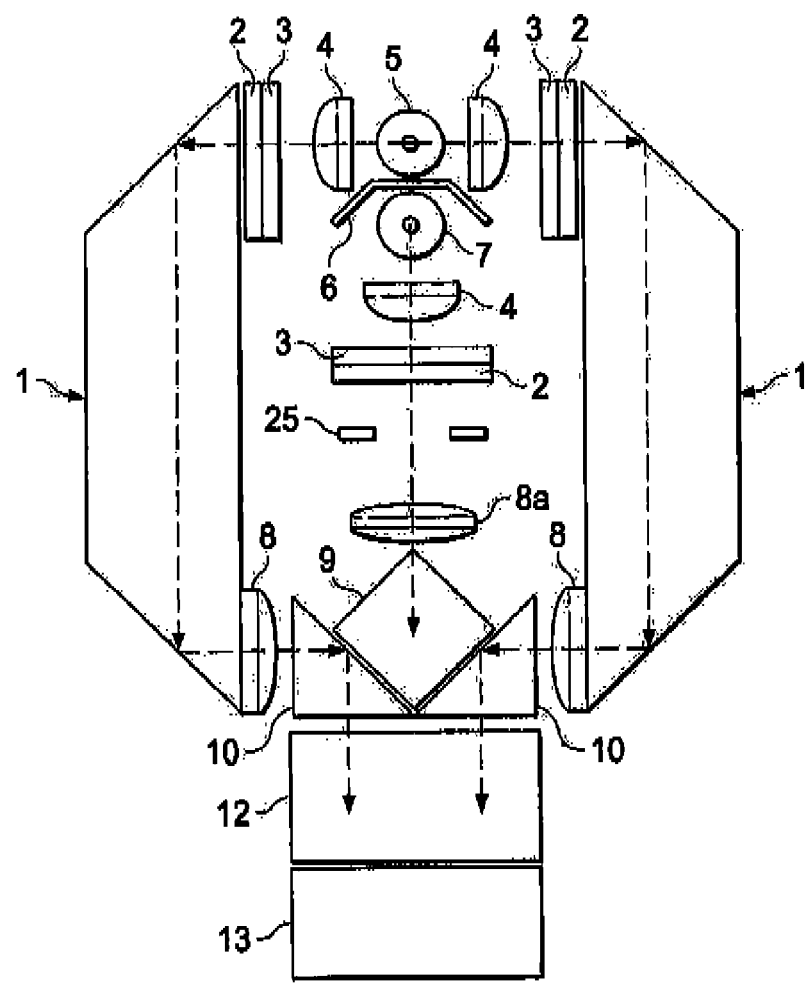
FIG. 1 is a view from the top of an embodiment of the illumination system showing the stereoscopic illumination system and the oblique illumination system. The lines with arrows represent the centers of the light beams from their source until they reflect against the beamsplitter (for stereoscopic) and against the full mirror (for oblique).
Figure 2:
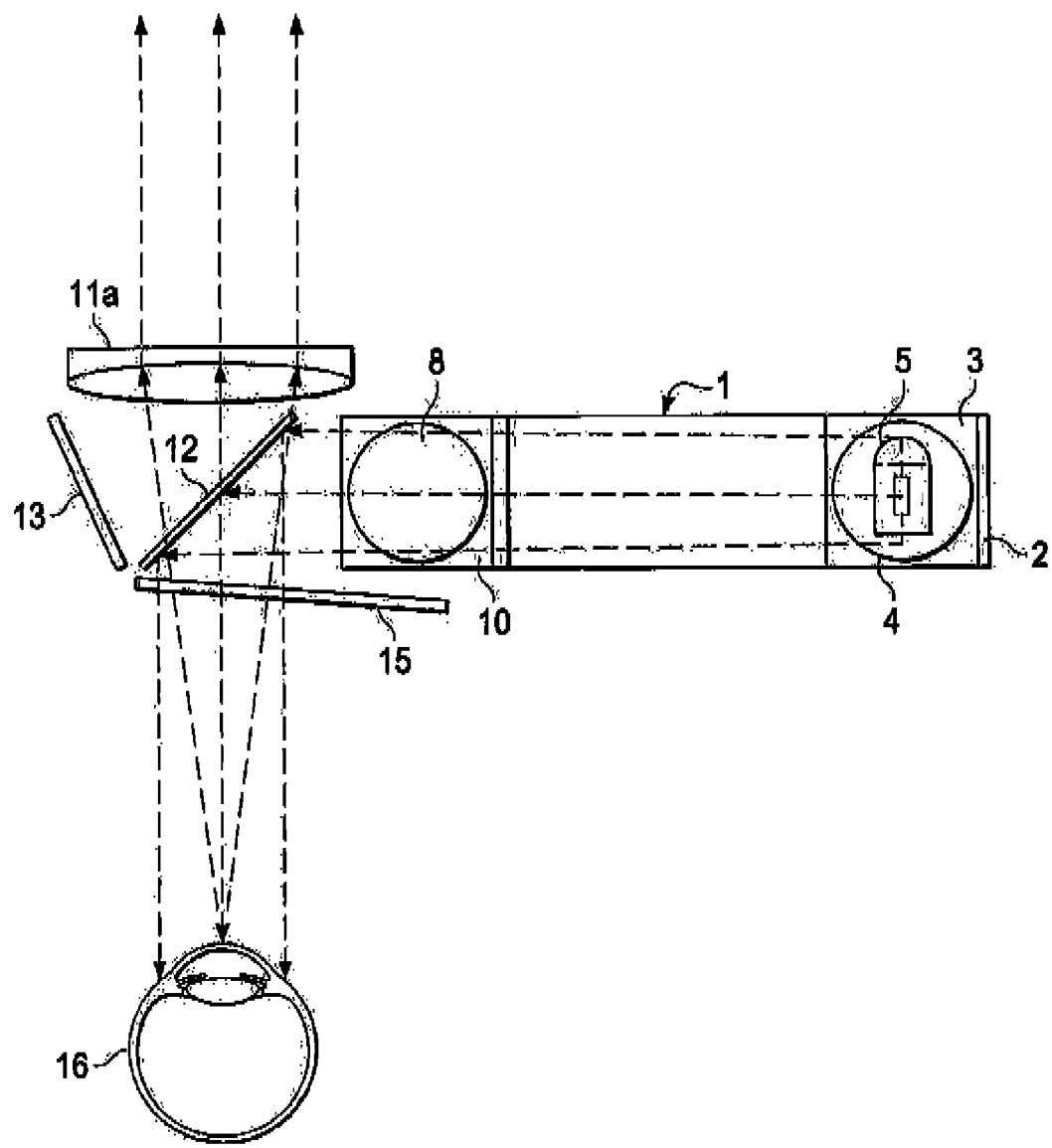
FIG. 2 is a side schematic view of one side of the embodiment of the stereoscopic illumination system. It shows a single collimated light beam illuminating the subject surface, in this instance an eye, and light from the eye's red reflex traveling through the objective lens toward the binoculars.
Figure 3:
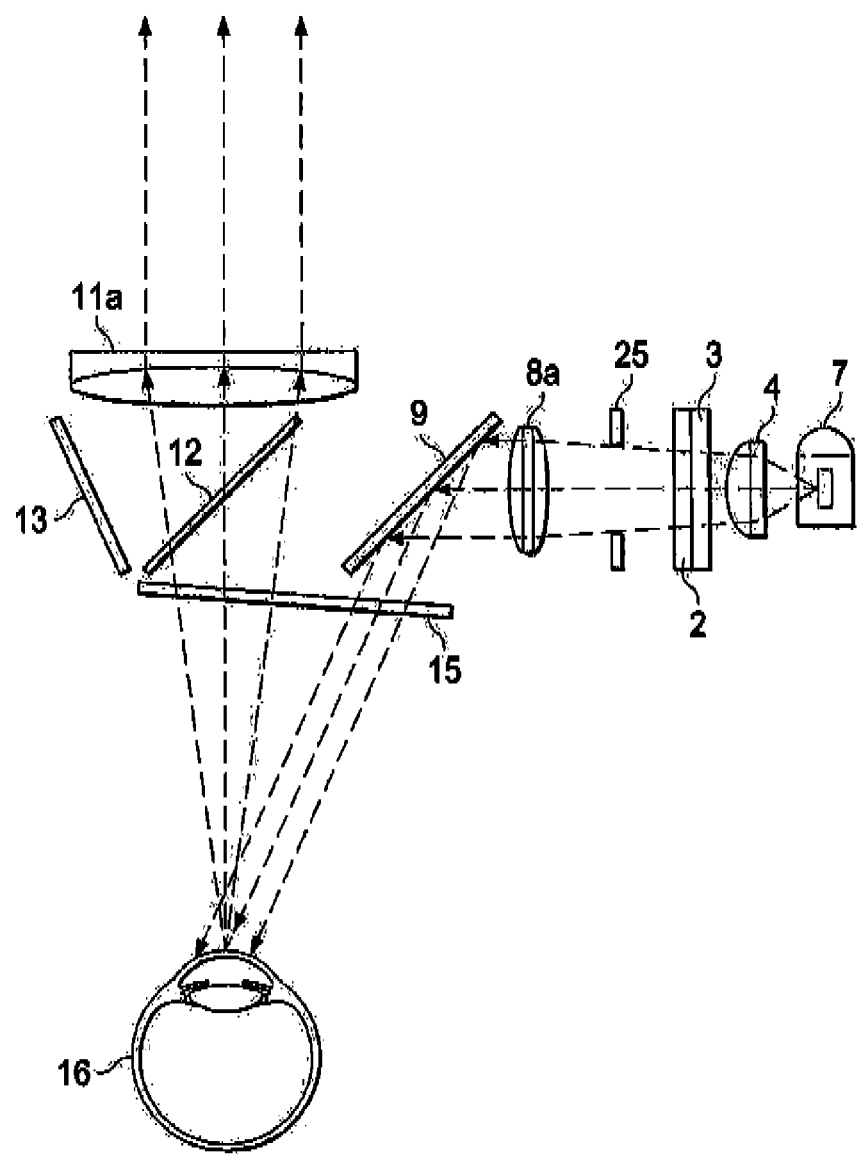
FIG. 3 is a side schematic view of an embodiment of the oblique illumination system, in which the light is offset at an angle oblique to the stereoscopic illumination system. It shows a light beam illuminating the subject surface, in this instance an eye, and light from the eye's red reflex traveling through the objective lens toward the binoculars.
Figure 4:
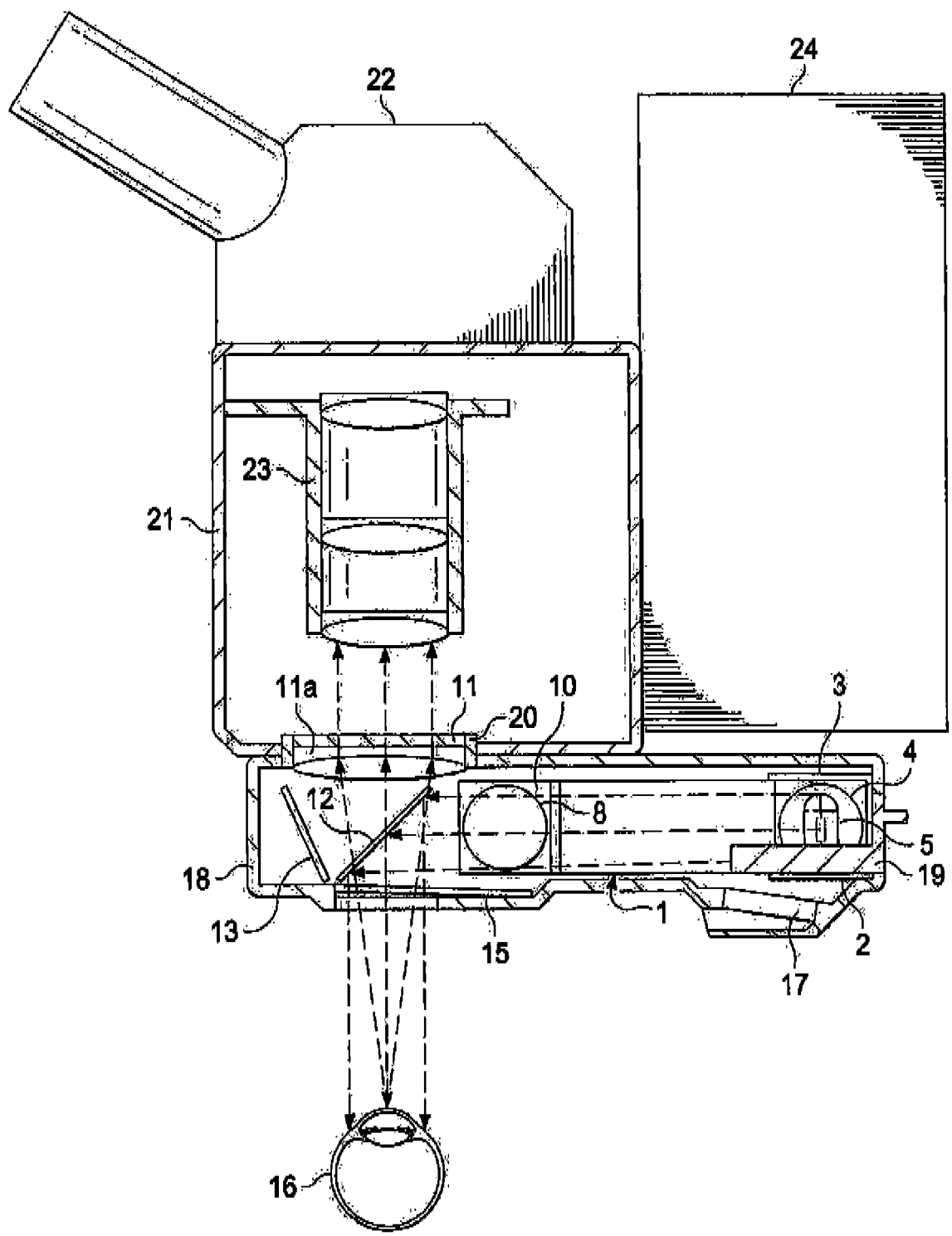
FIG. 4 is a side view of an embodiment of the system as a detachable module for an existing microscope, including a side schematic view of the stereoscopic illumination system and how the light beam illuminates the subject surface. It shows a collimated light beam illuminating the subject surface, in this instance an eye, and light from the eye's red reflex traveling through the objective lens toward the binoculars.
Figure 4A:
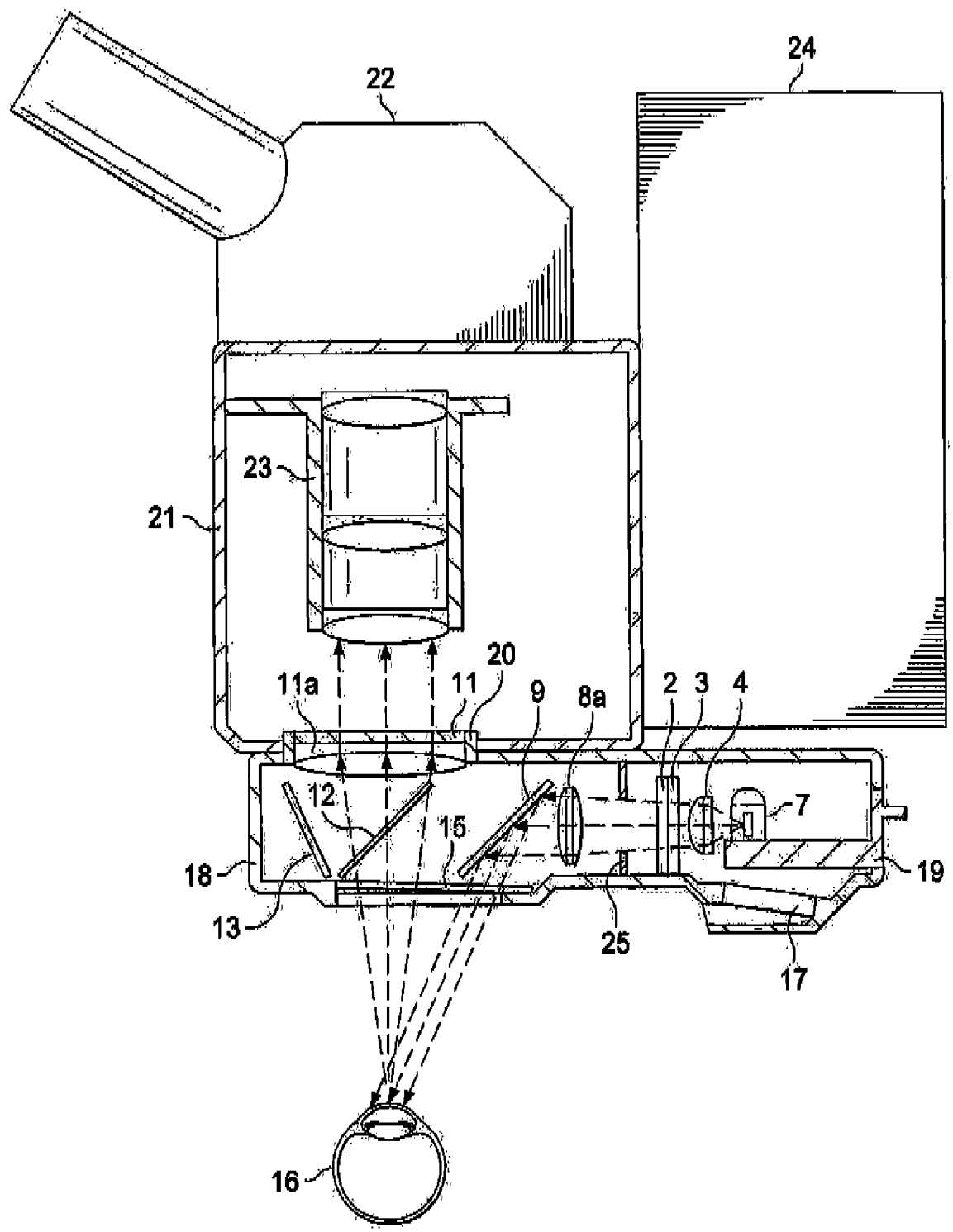
FIG. 4a is a side view of an embodiment of the illumination system as a detachable module for an existing microscope, including a side schematic view of the oblique illumination system and how the light beam illuminates the subject surface. It shows a light beam illuminating the subject surface, in this instance an eye, and light from the eye's red reflex traveling through the objective lens toward the binoculars.
Figure 5:
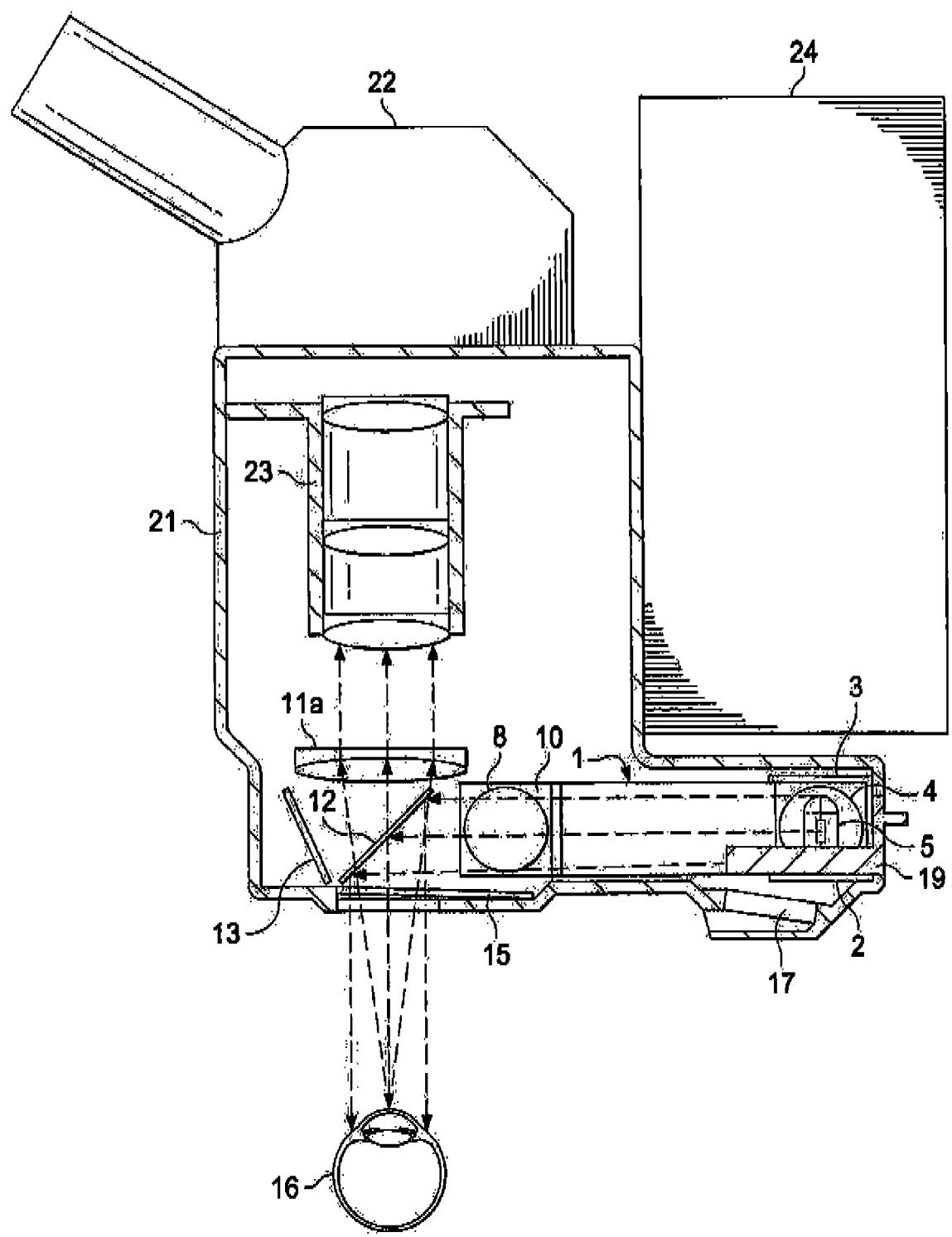
FIG. 5 is a side view of an embodiment of the illumination system as a module attached to an existing microscope, including a side schematic view of the stereoscopic illumination system and how the light beam illuminates the subject surface. It shows a collimated light beam illuminating the subject surface, in this instance an eye, and light from the red reflex traveling through the objective lens toward the binoculars.
Figure 5A:
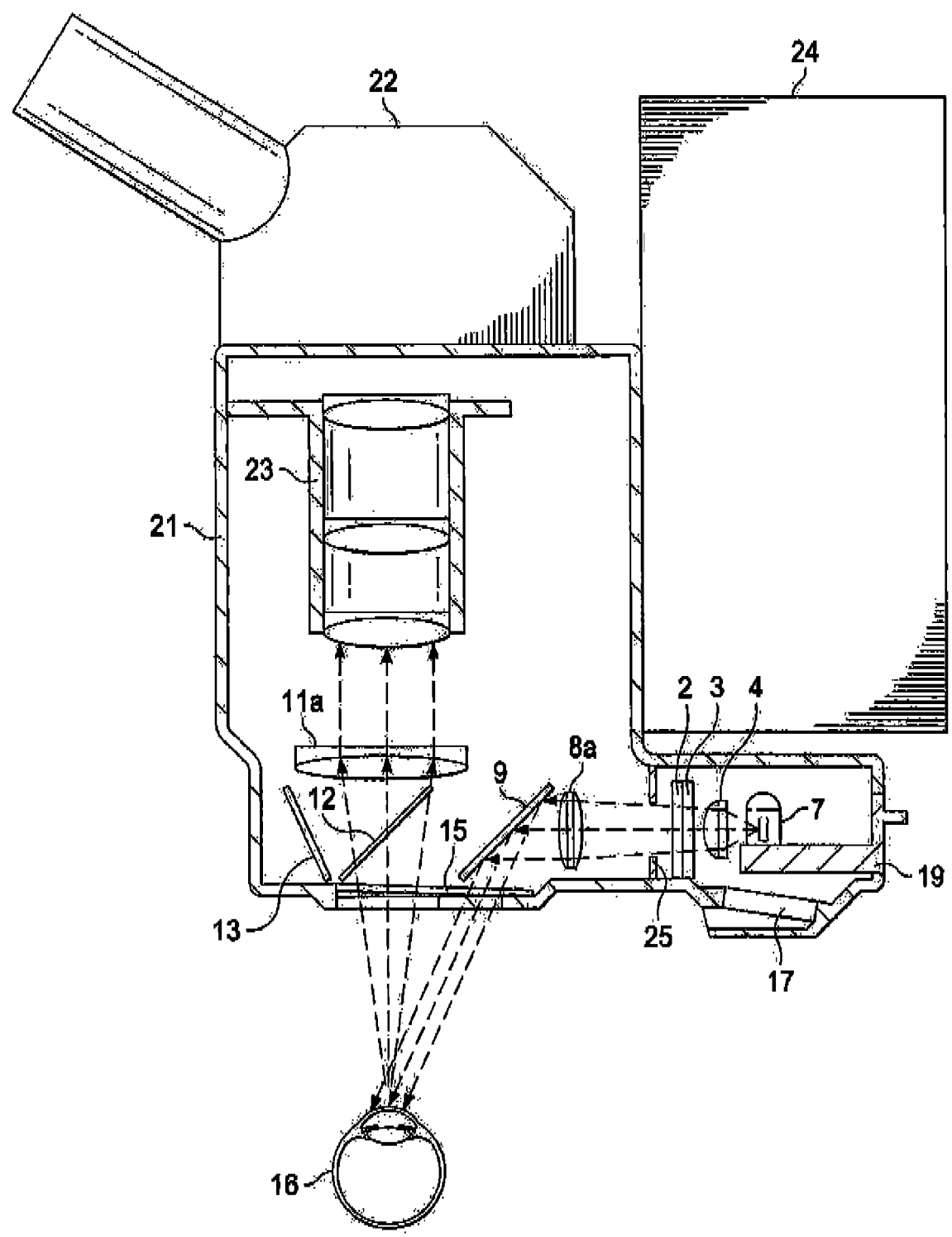
FIG. 5a is a side view of an embodiment of the illumination system as a module attached to an existing microscope, including a side schematic view of the oblique illumination system and how the light beam illuminates the subject surface. It shows a light beam illuminating the subject surface, in this instance an eye, and light from the red reflex traveling through the objective lens toward the binoculars.

An illumination system for a microscope is provided, the illumination system being below the objective lens 11a of the microscope. The illumination system contains two illumination sub-systems, the first being the stereoscopic sub-system which delivers two beams of collimated light (as defined herein) to the subject surface 16. These two beams of collimated light overlap on the subject surface 16 at least partially. The advantage of the stereoscopic collimated light is a better three dimensional view than produced by prior art illumination systems under similar circumstances. Compared to uncollimated light, delivering collimated light into a partially occluded opening allows a (a) greater quantity of light and (b) more direct light. The at least partial overlap 27 of the collimated light 29 and 30 allows the user viewing through binoculars 22 to view the subject surface 16 optimally with stereopsis. An additional illumination sub-system at an angle oblique to the stereoscopic sub-system is also provided, but the light for the oblique system need not be collimated.

A particular embodiment produces collimated light beams for each of the two stereoscopic light beams by passing light through an aspheric condensing lens 4 and then through a plano-convex lens positioned at the appropriate focal plane. The collimation can be accomplished at multiple points between the light source 5 and the subject surface 16 (e.g., before or after filtering, or before or after the beam is split).

The system can be built into an entire microscope or can be constructed as a module fitting onto an existing microscope. If constructed as a module, the module includes an objective lens 11a that replaces the objective lens of the microscope. Situated below the included objective lens 11a of the module type or of the objective lens 11a of the built-in type, are illumination components for directing light to the subject surface 16. The construction of the microscope may be altered substantially without affecting the illumination system.

In a further embodiment, one light source 5 produces two beams of light for the stereoscopic system which are directed by the following elements to the subject surface 16 as two collimated light beams. In another embodiment, the two collimated light beams are produced by two light sources, one for each light beam. The illumination components of the light source 5 for the stereoscopic system and the light source 7 for the oblique system are located inside the module or existing microscope and are separated by an opaque barrier 6. A beam from the stereoscopic light source 5 is collected by two condensing lenses 4 that gather and concentrate the light.

In another embodiment, each gathered and concentrated light beam passing through a condensing lens 4 is transmitted through an infrared filter 3 then through an ultraviolet filter 2 and then through a collimating lens 8. In one embodiment, a collimating lens 8 is a double convex lens (i.e., with a curved surface on both sides) with a positive focal length which, when used in conjunction with an upstream aspheric condensing lens 4 and positioned at the appropriate focal plane, produces collimated light.

In some embodiments, however, one light source 5 for the stereoscopic system is used to produce two beams of light in the following manner. A beam from each of two sides of the light source 5 is directed through a Dove prism 1 (bending light twice for a total of 180°) before reaching the collimating lens 8. After passing through the collimating lenses 8, each collimated light beam is then refracted by a 90° prism 10. Each column of collimated light exits its 90° prism 10 parallel to the other so that each strikes a beamsplitter 12 at an angle so that a portion of each column of collimated light is reflected downward toward the subject surface 16.

Figure 6:
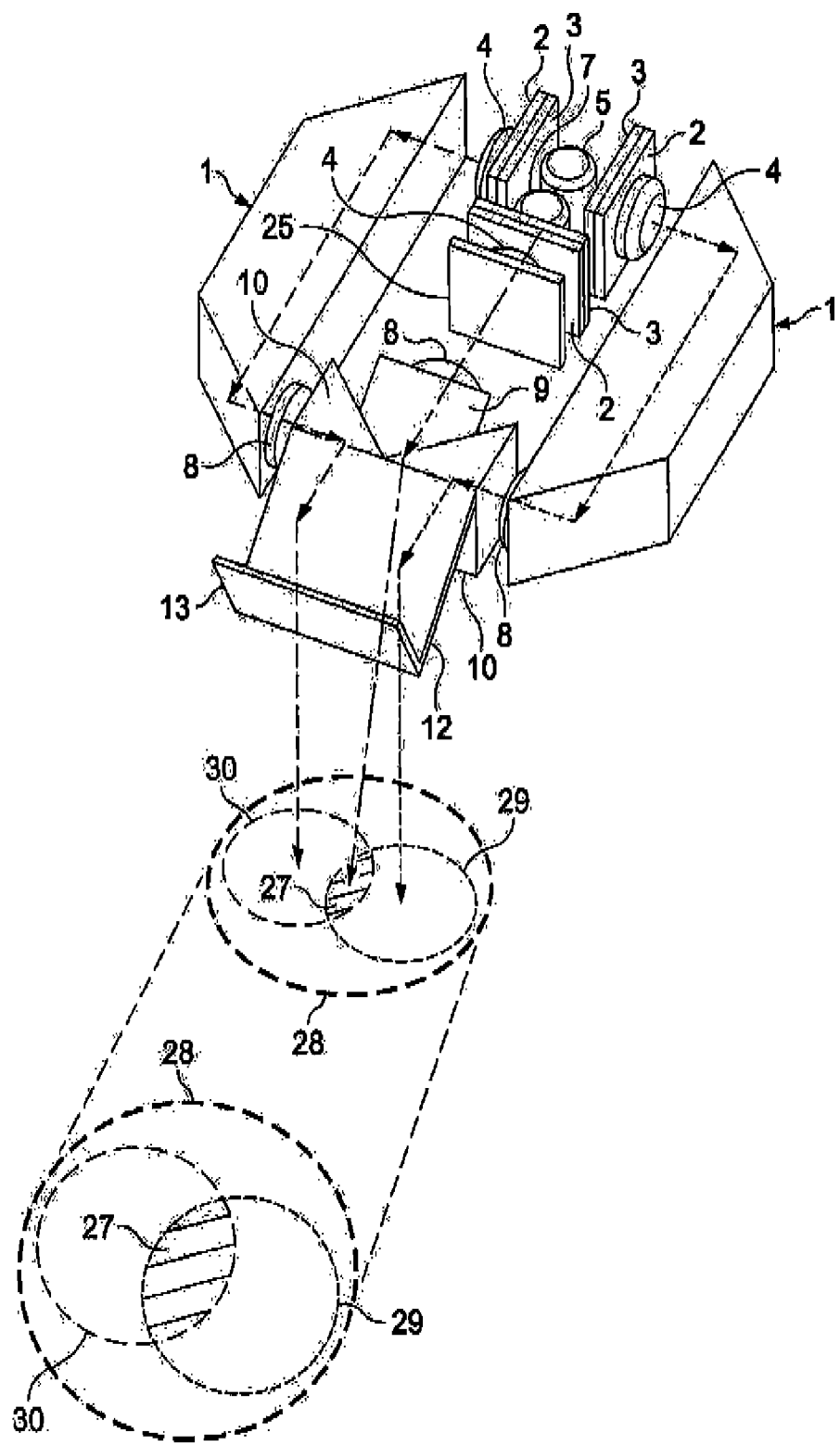
FIG. 6 is a 3 dimensional cutaway of an embodiment of the illumination system including the stereoscopic and the oblique illumination systems, the centers of the light beams, and the patterns of illumination on the subject surface.
Figure 7:
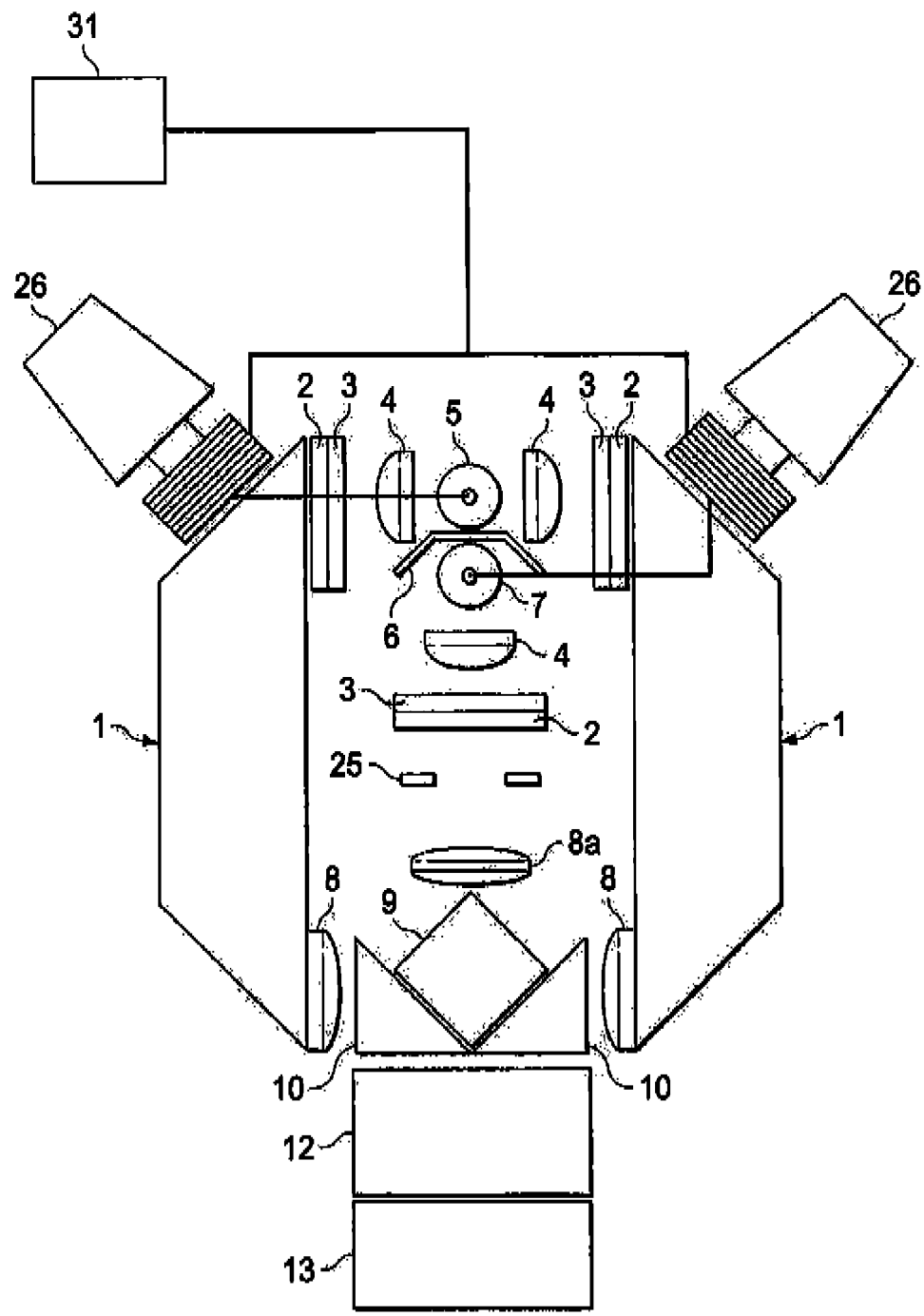
FIG. 7 depicts an embodiment of the illumination system with rheostats, for independent control of each illumination source, and their connections to an external power source.
Figure 8:
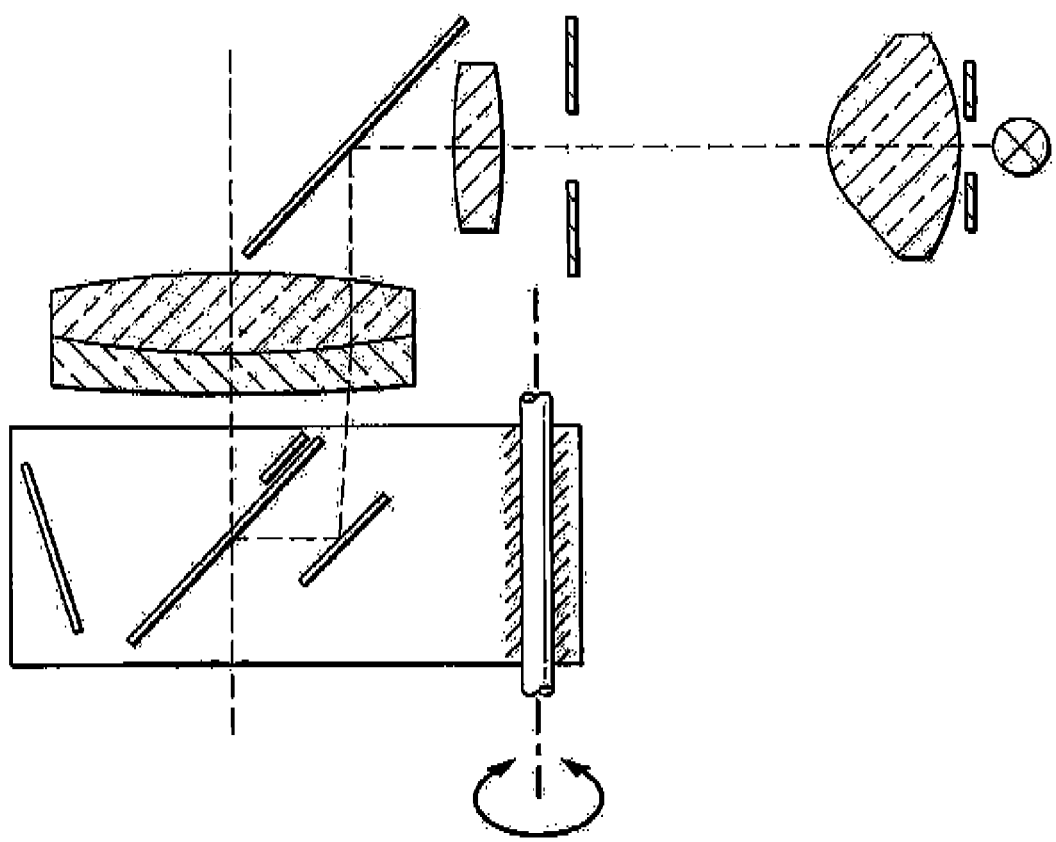
FIGS. 8 and 8a depict the illumination system described in U.S. Pat. No. 4,779,968.
Figure 8A:
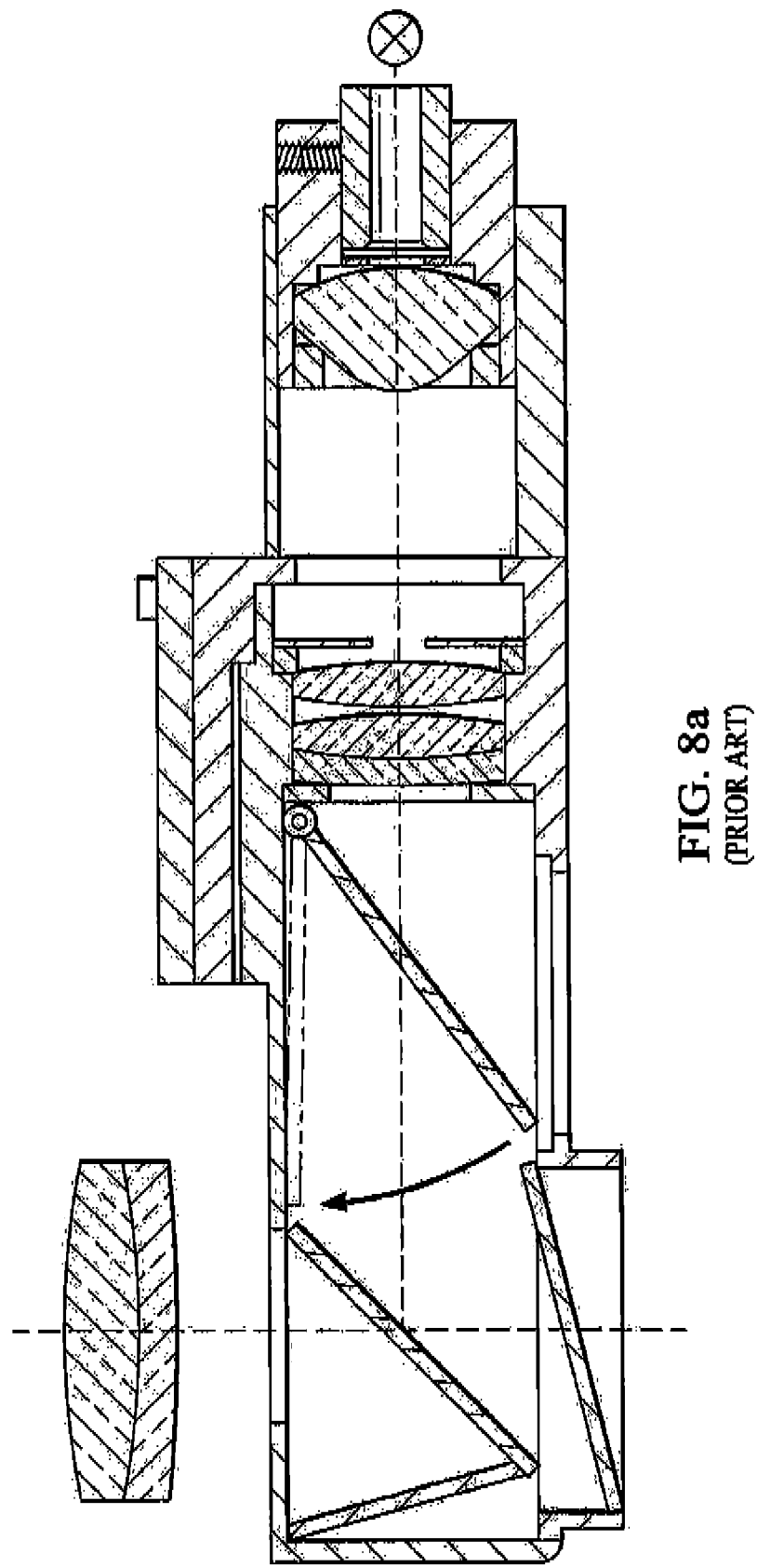
Figure 9:
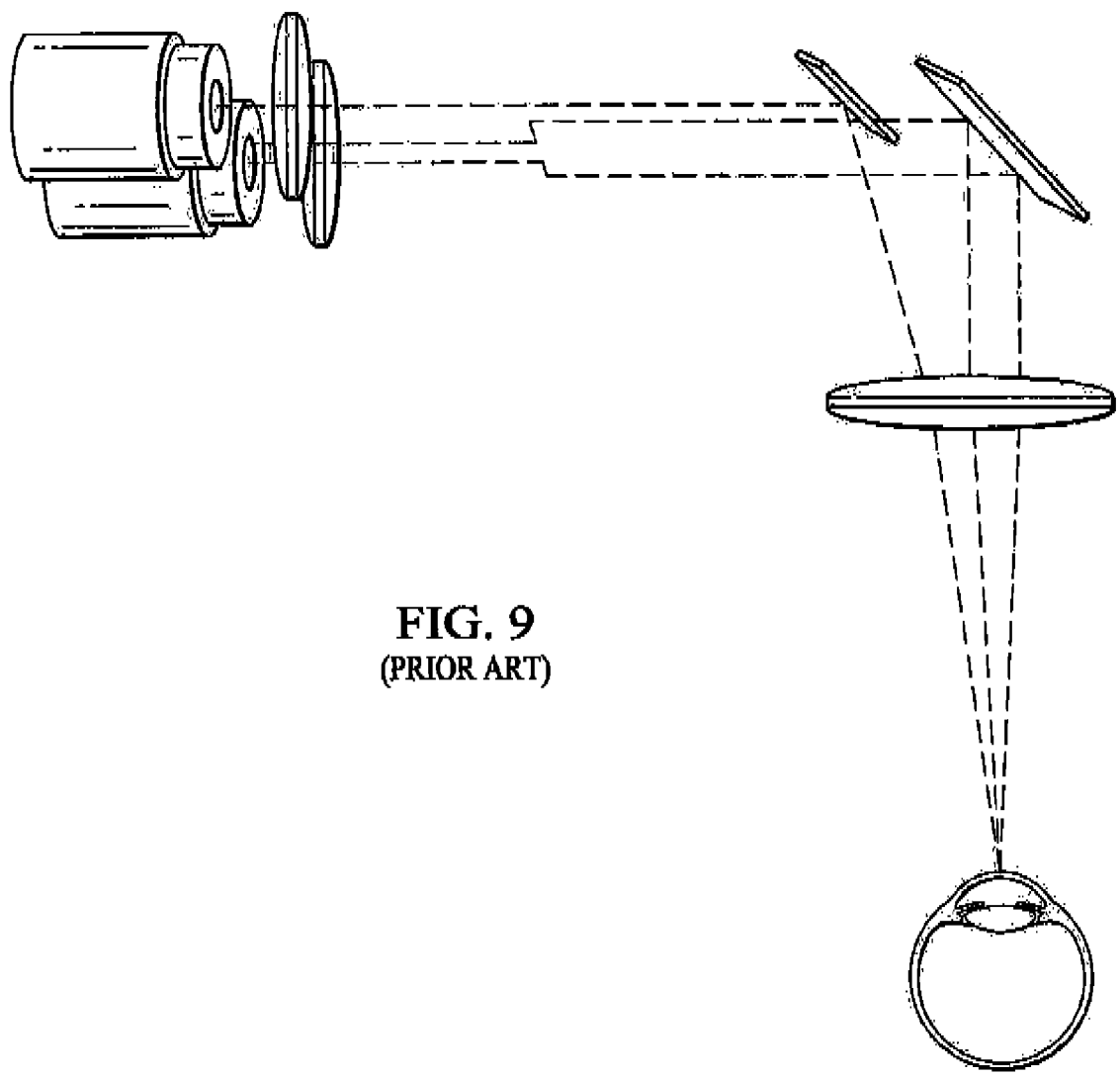
FIG. 9 depicts an illumination system believed to be the Zeiss Lumera microscope delivering two focused (uncollimated) beams to the subject surface through the objective lens.
Figure 10:
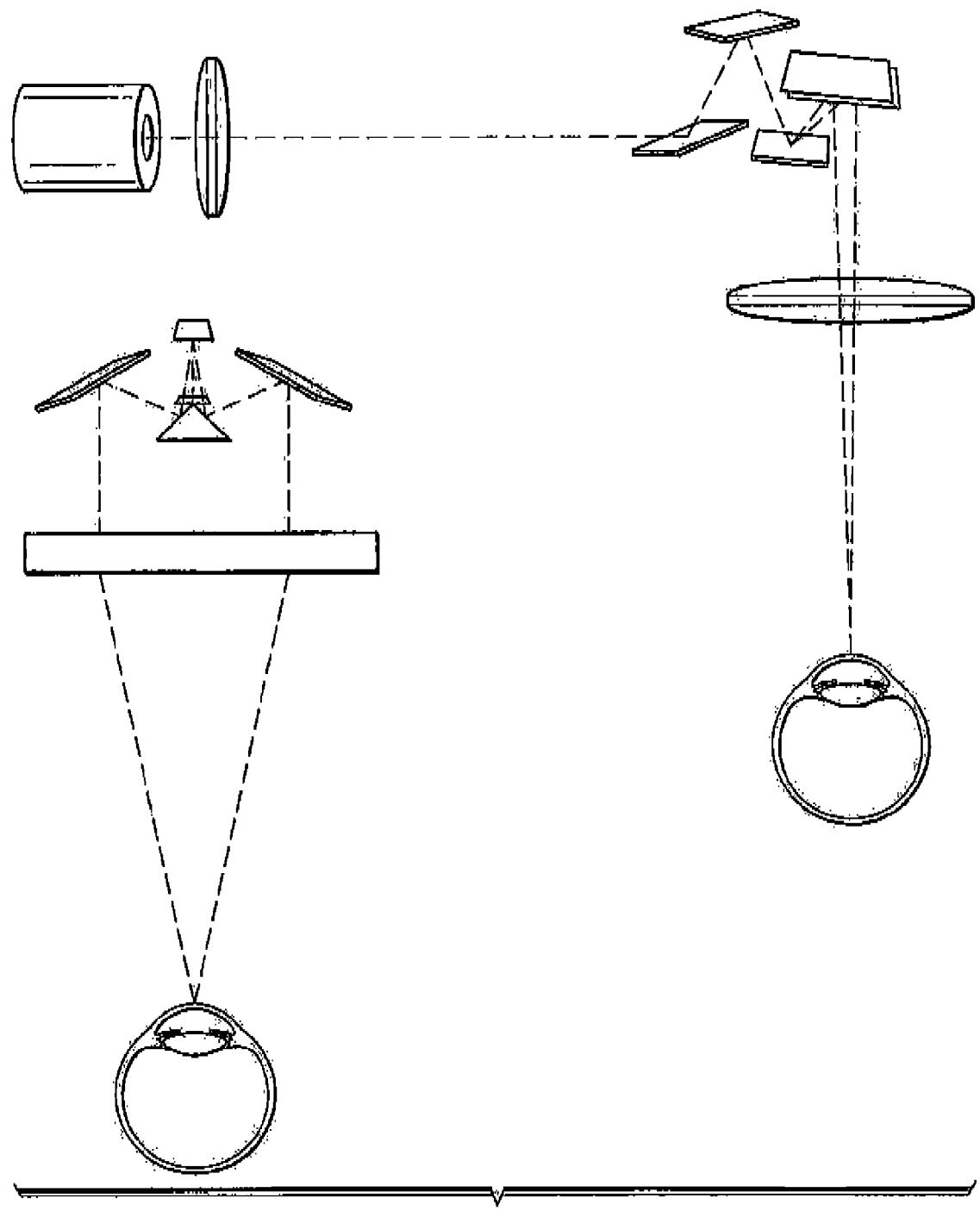
FIG. 10 depicts an illumination system from the Moller EOS 900 microscope delivering two focused (uncollimated) light beams through the objective lens to the subject surface.
Figure 11:
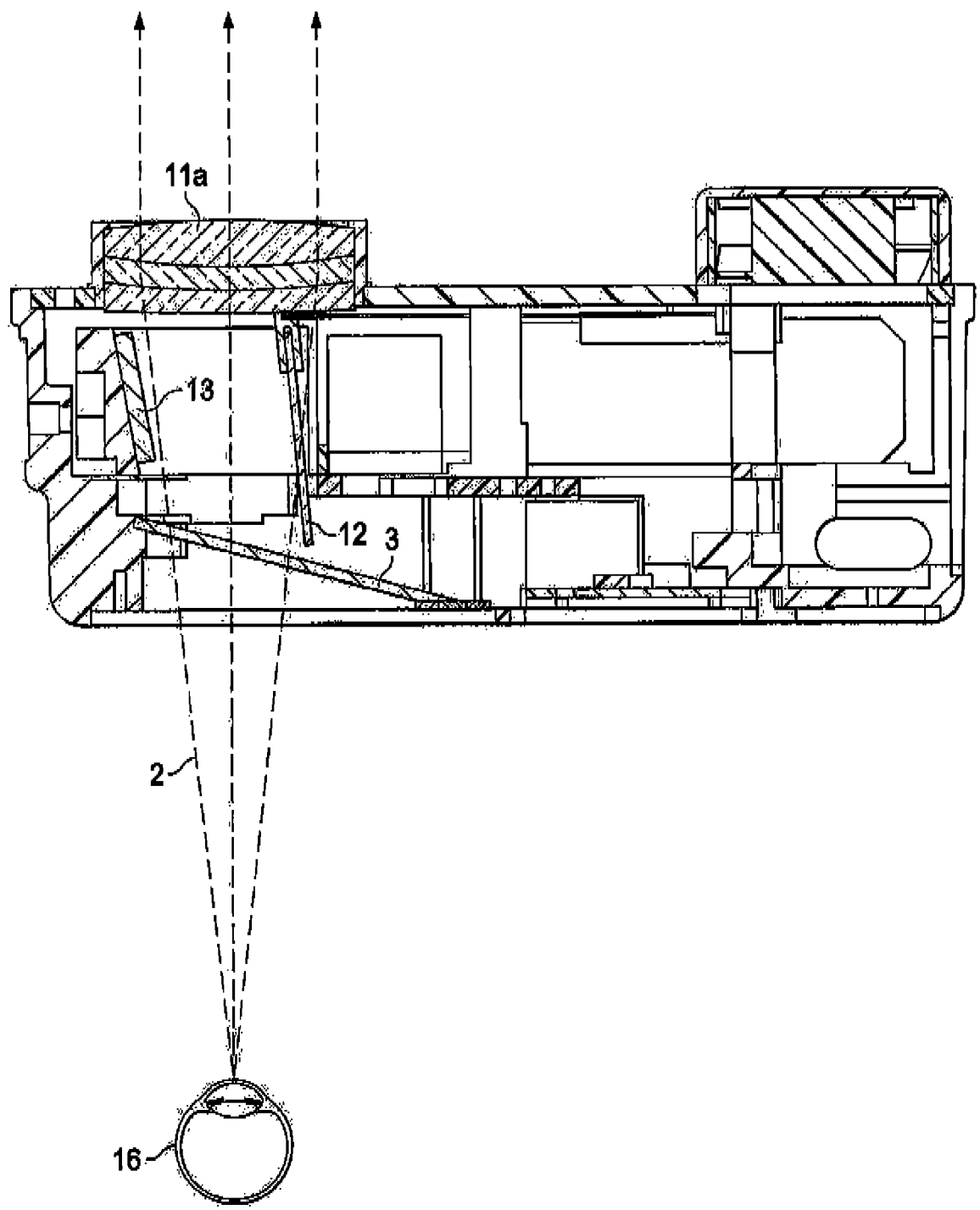
FIG. 11 is a side view of the microscope with disengagement of the retractable beamsplitter plate 31 for retinal surgery.

These columns of collimated light 29 and 30 reflected from the beamsplitter 12 downward to the subject surface 16 overlap each other at least partially at the stereoscopic illumination overlap 27 (as shown in FIG. 6) as dictated by the focal length of the included objective lens 11a. The portion of light from the collimated beams of light passing through the beamsplitter 12 is absorbed by an anti-reflective light absorber 13. In a preferred embodiment, the beamsplitter 12 splits the light in half, one half reflected to the subject surface 16 and the other half passes through the beamsplitter 12 to the anti-reflective light absorber 13. The beamsplitter 12 can be a half mirror or a mirror partially reflective in another fraction (e.g., three quarters reflective). The function of the beamsplitter 12 is to allow light to pass upward from the subject surface 16 to the binoculars 22 for the user. The collimated light beams are coaxial with the light transmitted to the binoculars 22. A plano glass cover 15 encloses the bottom portion of the module to protect the components from contaminants.

In some embodiments of the illumination system three beams of light are required, but they can be achieved in various ways. One way would be to use three light sources with each one having its own set of condensing 4 and collimating lenses 8. Another way would be to use two light sources, like the model depicted herein. This would utilize light emitting from two sides of one bulb for the stereo paths, and the second light source 7 for the oblique path. Another way would be to use one source. Light could be gathered from three sides of the bulb, condensed and collimated separately to form the three needed beams, or light could be gathered and then optically split into separate beams later on down the pathway. The significant advantage to using more than one light source, is the ability to adjust the illumination ratio between stereo and oblique light for optimal viewing. Using one source and having the ability to adjust light ratios would require mechanical shutters to block light accordingly. Another variance to the light source is to use fiber-optic light source. This merely removes the actual bulbs from the close proximity of the system and places them in a more remote location. The advantages of this are the ability to use higher power light sources that would not realistically fit in the module, heat generated by the bulbs being removed from proximity of the surgical procedure, and noise and air from the internal fan 17 also being removed to the remote site. One disadvantage with a fiber-optic system is light loss through the fiber-optic cable. Another variance for light sourcing is an LED (Light Emitting Diode) light source. It is also possible to have any combination of LED, bulb, and fiber-optic sources all in one system.

A light source for the oblique system 7 is located so that light from said the second light source is directed through a condensing lens 4 that gathers and concentrates the light from the light source 7. The gathered and concentrated light from the condensing lens 4 is transmitted through an infrared filter 3, and an ultraviolet filter 2 to a collecting lens 8a which collects diverging light from the condensing lens 4. The light passes through the collecting lens 8a and is reflected downward toward the subject surface 16 at an angle so that oblique illumination 28 of the subject surface 16 is accomplished. The oblique illumination 28 covers the entire visual field for both eyes of the user, assuming the objective is at a middle range or higher. The oblique illumination 28 can be reduced by an adjustable mechanical aperture 25 so that the illumination is centered in a smaller area of the subject surface 16, for instance the iris of an eye only, to eliminate glare to the user from light reflecting from the sclera of the eye.

The infrared filter 3 and ultraviolet filter 2 can be placed at any convenient position in the pathway between the light sources 5, 7 and the subject surface 16.

Rheostats 26 may control the intensity of the two light sources 5, 7 to control the amount of light projected to the subject surface 16.

A cooling fan 17 may be mounted in close proximity to the bulb tray 19 or other light sources in the illumination system.

The housing 18 of the modular component may contain a fitting for connection to an existing microscope. This fitting may attach at the existing microscope's objective lens receptacle 11 after the existing microscope's objective lens is removed. This fitting locks the module housing 18 in place in the existing microscope's objective lens receptacle 11. A particular embodiment of this fitting is an attachment ring 20 which screws or otherwise mounts onto the existing microscope.

For the full microscope containing the system, the binoculars 22 are in communication with zoom optics 23 which are housed in the microscope body 21 and are in communication with the objective lens 11a. There is a focus drive housing 24.

The built-in system may be completely enclosed in the body of the microscope below the zoom system and the objective lens 11a.

Ancillary optics 9, such as mirrors and prisms, are used to refract the light so that the projected beams exit the system at proper angles. They could also be used to split a single light beam into two light beams. This could be done if only one light source was being used, or if a fiber-optic system was used and the incoming beam needed to be converted to two or three beams. This placement of the ancillary optics 9 for light redirection or splitting along the pathway is irrelevant to the function as long as the beams are directed to the proper locations, but keeping in mind losses that occur at each light interface.

There are numerous combinations that could be achieved using one or more of the same or different light sources, mirrors and prisms for directing light around inside the system, using prisms to split beams at any point along the light pathway if there are not enough beams from light sources, using or not using a mechanical shutter for illumination intensity control, placement of the ultraviolet 2 and infrared 3 filters, and even the direction and angle at which the oblique light illuminates the field. Ultimately, these variances if done properly, all result in two collimated stereo illumination beams hitting the beamsplitter 12 set at a forty-five degree angle in the direct path of the optical viewing pathways of a microscope, and a third oblique illumination beam hitting the subject surface 16 at some offset angle with the ability to control the levels and/or ratios of said illumination.

One embodiment directs illumination light rays onto the patient from one light source, but with three illumination pathways—the two co-axial 90 degree pathways, and one oblique eight degree pathway. The two 90 degree pathways are directed down to the patient via a beamsplitter plate glass 12 directly in-line with the stereo microscope optical pathways, creating the true dual co-axial illumination. This provides optimal red reflex or retinal reflex primarily for cataract surgery, but in other surgical settings the bright full red-reflex is not desired. In one embodiment of the system, the surgeon has the ability then to turn off, via shutter, the 90 degree co-axial illumination pathways. At this point the surgeon is solely utilizing the eight degree illumination for surgery. When the microscope is being used in this state, the beamsplitter 12 is no longer needed, as there is no 90 degree illumination. To maximize light transfer through the system, the beamsplitter 12 is moved out, or disengaged, from the stereo microscope optical pathways. Then when the 90 degree co-axial illumination is required again, the user can re-engage the beamsplitter 12 plate and 90 degree co-axial illumination.

Retinal surgery requires the use of a surgical microscope. The microscope is equipped with a device for magnifying the retina so that the surgeon sees a large view of the operative site. However, the normal illumination of the surgical microscope is not used in retinal surgery. A small fiberoptic pic about 1 mm in diameter can be inserted through the sclera and into the vitreous body for direct illumination of the retinal surface. The surgeon holds this fiberoptic pic such that light exiting the tip of the fiberoptic pic is directed toward the retinal tissue on which the operating instruments are utilized. Since the normal illumination of the microscope is not utilized and is in fact turned off, and since only the relatively low illumination from the fiberoptic pic illuminating the retinal surface is seen by the surgeon, it is to the surgeon's advantage to have an optical system that does not significantly decrease the light from the retina. It can therefore be desirable, in one embodiment, to retract the beamsplitter plate from the optical system for retinal surgery. The present invention accomplishes this goal by allowing the beamsplitter plate to be rotated out of the light beam path, thus allowing 100% of the reflected light from the retina to enter the optical system of the surgical microscope and be transmitted to the user. Thus, when co-axial illumination is not desired, a retractable beamsplitter plate 31 is disengaged to slightly beyond a vertical position. In this position there is no light loss from having the retractable beamsplitter plate 31 incident to the light rays 2 entering the microscope system. By disengaging the retractable beamsplitter plate 31 a 50% increase in light transfer efficiency can be achieved, thus allowing more light to reach the surgeon. The beamsplitter is thus retractable, and in this way the same microscope can be used, on the one hand, in cataract and other surgery using the illumination system and with the retractable beamsplitter engaged, on the other hand, in retinal and other surgery without using the illumination system and with the retractable beamsplitter disengaged.

CONCLUSION

It is to be understood that any given elements of the disclosed embodiments of the invention may be embodied in a single structure, a single step, a single substance, or the like. Similarly, a given element of the disclosed embodiments may be embodied in multiple structures, steps, substances, or the like. The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein.

What is claimed is:

1. A microscope illumination system comprising:
an objective lens through which light reflected from a subject surface travels;
a stereoscopic illumination system configured to deliver a plurality of collimated light beams such that:
the collimated light beams reach a line of sight at a location between the objective lens and the subject surface; and
the collimated light beams at least partially overlap at the subject surface; and
a beamsplitter configured to move to a first position to allow the collimated light beams to reach the subject surface and move to a second position to prevent the collimated light beams from reaching the subject surface.

2. The system of claim 1, further comprising:
an oblique illumination system configured to deliver an oblique light beam at an angle oblique to the collimated light beams.

3. The system of claim 1:
further comprising an oblique illumination system configured to deliver an oblique light beam at an angle oblique to the collimated light beams; and
wherein the oblique light beam reaches the line of sight at a location between the objective lens and the subject surface.

4. The system of claim 1:
further comprising an oblique illumination system configured to deliver an oblique light beam at an angle oblique to the collimated light beams; and
wherein the oblique light beam overlaps the collimated light beams at the subject surface.

5. The system of claim 1, further comprising:
an oblique illumination system configured to deliver an oblique light beam at an angle oblique to the collimated light beams; and
ancillary optics configured to control the illumination ratio of the oblique light beam and the collimated light beams.

6. The system of claim 1, wherein the beamsplitter is configured to move by rotating.

7. The system of claim 1, further comprising:
a light absorber configured to receive a portion of the collimated light beams that pass through the beamsplitter.

8. A microscope illumination system comprising:
a stereoscopic illumination system configured to deliver a plurality of collimated light beams that at least partially overlap at a subject surface;
an oblique illumination system configured to deliver an oblique light beam at an angle oblique to the collimated light beams; and
a beamsplitter configured to move to a first position to allow the collimated light beams to reach the subject surface and move to a second position to prevent the collimated light beams from reaching the subject surface.

9. The system of claim 8:
further comprising an objective lens through which light reflected from the subject surface travels; and
wherein the collimated light beams reach a line of sight at a location between the objective lens and the subject surface.

10. The system of claim 8:
further comprising an objective lens through which light reflected from the subject surface travels; and
wherein the oblique light beam reaches a line of sight at a location between the objective lens and the subject surface.

11. The system of claim 8, wherein the oblique light beam overlaps the collimated light beams at the subject surface.

12. The system of claim 8, further comprising:
ancillary optics configured to control the illumination ratio of the oblique light beam and the collimated light beams.

13. The system of claim 8, wherein the beamsplitter is configured to move by rotating.

14. The system of claim 8, further comprising:
a light absorber configured to receive a portion of the collimated light beams that pass through the beamsplitter.

\* \* \* \* \*